United States Patent
Grassauer et al.

(10) Patent No.: US 9,993,512 B2
(45) Date of Patent: Jun. 12, 2018

(54) USE OF ESCIN

(71) Applicant: MARINOMED BIOTECHNOLOGIE GMBH, Vienna (AT)

(72) Inventors: Andreas T. Grassauer, Vienna (AT); Eva Prieschl, Vienna (AT)

(73) Assignee: MARINOMED BIOTECHNOLOGIE GMBH, Vienna (AT)

(*) Notice: Subject to any disclaimer, the term of this patent is extended or adjusted under 35 U.S.C. 154(b) by 0 days. days.

(21) Appl. No.: 15/281,635

(22) Filed: Sep. 30, 2016

(65) Prior Publication Data
US 2017/0014465 A1 Jan. 19, 2017

Related U.S. Application Data

(63) Continuation of application No. 12/376,419, filed as application No. PCT/EP2007/006870 on Aug. 3, 2007, now abandoned.

(30) Foreign Application Priority Data

Aug. 4, 2006 (EP) .................................... 06450109

(51) Int. Cl.
*A61K 31/704* (2006.01)
*A61K 36/77* (2006.01)
*A61K 9/00* (2006.01)

(52) U.S. Cl.
CPC ............ *A61K 36/77* (2013.01); *A61K 9/0014* (2013.01); *A61K 31/704* (2013.01)

(58) Field of Classification Search
None
See application file for complete search history.

(56) References Cited

U.S. PATENT DOCUMENTS

| | | | |
|---|---|---|---|
| 6,504,010 B1 | 1/2003 | Wang et al. | 435/325 |
| 6,509,448 B2 | 1/2003 | Wang et al. | 530/387.9 |
| 6,630,305 B1 | 10/2003 | Xu et al. | 435/6 |
| 6,759,515 B1 | 7/2004 | Xu et al. | 435/6 |
| 6,800,746 B2 | 10/2004 | Xu et al. | 536/23.1 |
| 6,858,204 B2 | 2/2005 | Henderson et al. | 424/184.1 |
| 6,894,146 B1 | 5/2005 | Xu et al. | 435/6 |
| 6,943,236 B2 | 9/2005 | Xu et al. | 530/350 |
| 7,033,827 B2 | 4/2006 | Xu et al. | 435/320.1 |
| 7,049,063 B2 | 5/2006 | Wang et al. | 435/6 |

FOREIGN PATENT DOCUMENTS

| | | |
|---|---|---|
| DE | 3402259 | 8/1985 |
| DE | 3445324 | 6/1986 |
| DE | 1676561 | 7/2006 |
| EP | 0550008 | 7/1993 |
| JP | A 5-339153 | 12/1993 |

OTHER PUBLICATIONS

Chinese Office Action, issued in Chinese Patent Application No. 200780029119.X, dated Aug. 12, 2010 (English translation).
Dattner, "From medical herbalism to phytotherapy in dermatology: back to the futuer," *Dermatologic Therapy*, 16 (2): 106-113, 2003.
Dunphy and Gardiner, "NK cells and psoriasis," *Journal of Biomedicine and Biotechnology*, 2011;2011:248317. Epub May 26, 2011. 10 pages.
European Search Report, issued in Int. App. No. EP 06450109, dated Jun. 21, 2007.
Haosheng et al., "Progress of study in functions of pharmacological mechanisms of Aescin," *World Science and Technology—Modernization of Traditional Chinese Medicine and Material Medica*, 6:45-46, 72, 2004 (English abstract).
International Search Report and Written Opinion, issued in Int. App. No. PCT/EP2007/006870, dated Feb. 11, 2008.
Matsuda et al., "Anti-inflammatory effects of escins Ia, Ib, IIa, and IIb from horse chestnut, the seeds of aesculus hippocastanum L.," *Bioorganic & Medicinal Chemistry Letters*, 7 (13): 1611-1616, 1997.
Munoz et al., "Occupational Asthma Related to Aescin Inhalation," *Annals of Allergy* 96(36): 2006, 494-496.
Regoczy, Machine Translation of DE 3402259, dated Sep. 10, 2012.
Sirtori, "Aescin: pharmacology, phamacokinetics, and therapeutic profile," *Pharmacological Research*, 44 (3): 183-193, 2001.
Tiffany et al., "Horse chestnut:a multidisciplinary clinical review," *J. of Herbal Phamacotherapy*, 2 (1): 71-85, 2002.
Van Cauwenberge, et al., "Consensus Statement on the Treatment of Allergic Rhinitis," *Allergy*, 55: 2000, 116-134.
World Health Organization, "WHO monographs on selected medicinal plants," *World Health Organization*, http://whqlibdoc.who.int/publications/2002/9241545372.pdf, 137-148, retrieved on Jan. 1, 2008.
WebMD, "Decongestants for Sinusitis," also available at http://www.webmd.com/a-to-z-guides/decongestants-for-sinusitis; last updated Aug. 3, 2010.
Xiao and Wei, "Effects of beta-Aescin on the expression of nuclear factor-kappaB and tumor necrosis factor-alpha after traumatic brain injury in rats," *J. Zhejiang Univ. SCI.*, 6b (1): 28-32, 2005.

*Primary Examiner* — Shaojia A Jiang
*Assistant Examiner* — Bahar Craigo
(74) *Attorney, Agent, or Firm* — Norton Rose Fulbright US LLP

(57) ABSTRACT

The present invention provides the use of escin for the manufacture of a pharmaceutical preparation for the treatment diseases mediated or caused by activated granulocytes, preferably a type I or type III allergy or septic shock.

8 Claims, 2 Drawing Sheets

USE OF ESCIN

CROSS REFERENCES WITH RELATED APPLICATIONS

This application is a continuation of U.S. patent application Ser. No. 12/376,419, filed Feb. 4, 2009, which is a national phase application under 35 U.S.C. § 371 of International Application No. PCT/EP2007/006870, filed Aug. 3, 2007, which claims priority to European Patent Application No. 06450109.1, filed Aug. 4, 2006. The contents of the aforementioned applications are incorporated herein by reference.

BACKGROUND OF THE INVENTION

The present invention relates to the field of immunology.

An allergy can refer to several kinds of unwanted immune reactions including Type I and Type III hypersensitivities. In both types granulocytes, a subset of leukocytes, are involved in the pathogenesis of these diseases. Leukocytes consist of different cell types that all origin from stem cells in the bone marrow. They are further subdivided into lymphocytes (T-cells, B-cells, natural killer cells), myeloid cells (monocytes, macrophages) and granulocytes (eosinophils, neutrophils, and basophils). Mast cells are closely related to basophils and are often regarded as the tissue residing type of a granulocyte. Therefore, in the following granulocytes are defined as eosinophils, neutrophils, basophils, and mast cells. Granulocytes are part of the innate immune response, an unspecific reaction towards pathogens, such as bacteria. This is also reflected by the fact that lipopolysacharide (LPS, component of bacterial cell wall) activation of granulocytes results in a pronounced release of cytokines, such as tumour necrosis factor alpha (TNF-alpha). Activation of granulocytes with either IgE- (type I allergy) or IgG complexes (type III allergy), results in a strong and fast reaction against otherwise innocuous agents (pollen, food, reactions against own structures and tissues such in autoimmune diseases). Mast cells and basophils are the cellular basis for type I allergies (IgE-mediated allergies via the Fc☐RI), neutrophils are involved in type III allergies (immune complex mediated reactions, via the Fc☐RIII) including autoimmune diseases such as psoriasis, arthritis, immune thrombocytopenia (ITP), autoimmune hemolytic anemia (AHA) and systemic lupus erythematosus (SLE), and contributes to other autoimmune diseases such as rheumatoid arthritis (RA), type I diabetes and multiple sclerosis. Allergies of both types can result in symptoms as benign as a runny nose, to severe chronic diseases and also to life-threatening anaphylactic shock or septic shock.

Type I allergies are commonly treated by corticosteroids (cortisone), anti-histamines, ephinephrine, theophylline or mast cell stabilizers. These compounds block the action of allergic mediators, preventing activation of cells and degranulation processes. These drugs help alleviate the symptoms of allergy but play little role in chronic alleviation of the disorder. All of these therapeutical classes have quite substantial side-effects especially after long-term use. Allergies have an increasing incidence in the western hemisphere with about 20% of the population being affected now. A review and recommendation for treatment of allergic rhinitis has been published by the British National Prescribing Center: MeReC Bulletin Volume 9, Number 3, 1998. Another treatment form of allergies involves the intravenous injection of monoclonal anti-IgE antibodies. Hyposensitization is a form of immunotherapy where the patient is gradually vaccinated against progressively larger doses of the allergen in question. This can either reduce the severity or eliminate hypersensitivity altogether. It relies on the progressive skewing of IgG production, as opposed to the excessive IgE production seen in hypersensitivity type I cases. Allergic diseases type III are commonly treated by steroids, non-steroid anti-inflammatory drugs, methotrexate, and TNF-alpha blocker (receptor analogs or antibodies).

Some autoimmune diseases such as psoriasis or blistering diseases are further complicated by secondary infections of the skin. In contrast to acute injuries of the skin, where antibiotics are usually applied, secondary infections that are the result of chronic disorder such as psoriasis are often left untreated. As a consequence the inflammatory process is worsened and the disease progresses. In both types of hypersensitivities, however, there is still a strong medical need as many of these substances are not suited for a chronic application or the treatment is too expensive for broad use (biological substances). Psoriasis or rheumatoid arthritis belong to the most common autoimmune diseases with 1-2% of the population being affected.

Sirtori (Pharmacological Research 44 (3) (2001): 183-193) discloses an anit-inflammatory effect of aescin which is effected by the reduction of vascular permeability which can reduce the density of leucocytes in affected tissue.

Matsuda et al. (Bioorganic & Medicinal Chemistry Letters 7 (13) (1997): 1611-1616) mention an antiinflammatory effect of isolated escin compounds from horse chestnut which is based on vascular constriction measured through an anti-swelling effect in carragenin induced oedemas in rats.

Dattner (Dermatologic Therapy 16 (2003): 106-113) discusses horse chestnuts in the field of herbal medicine with an anti-inflammatory and vasoprotective effect. An elastase-inhibitory activity is attributed to escin.

SUMMARY OF THE INVENTION

A goal of the present invention is to provide further medications, which are effective against diverse immunological diseases that are based on a hyper-response of granulocytes.

The present invention provides the use of escin for the manufacture of a pharmaceutical preparation (or a medicament) for the treatment diseases mediated or caused by activated granulocytes, preferably a type I or type III allergy or septic shock. Leukocytes such as granulocytes play a role in almost all diseases as the body's defense system. Some symptoms of any disease may be related to the direct effector functions of the granulocytes. The term "diseases caused or mediated by granulocytes" is to be understood in the context of the origin of the disease and not only the symptoms of the disease. The diseases to be treated by the pharmaceutical preparation are therefore related to an aberrant or excessive function of granulocytes. Allergies are caused by contact to an allergen (external or internal) which mediates an excessive granulocyte reaction which can be considered as the cause of the disease since the allergen by itself would be harmless. Therefore the present invention relates to the use of escin for the manufacture of pharmaceutical preparation for the treatment of a disease, wherein the origin of the disease is mediated or caused by activated granulocytes.

Also provided is escin for the treatment (or prevention, prophylactic treatment) of diseases mediated or caused by activated granulocytes or for the treatment (or prevention) of a disease, wherein the origin of the disease is mediated or caused by activated granulocytes. In particular embodiments this does not extend to the treatment of inflammation or of oedemas. Prevention should not be interpreted to an absolute success in the sense that a patient can never develop an associated disease but to the reduction of the chance of developing the disease in a prophylactic treatment.

In particular embodiments the granulocytes are hyperactivated. This excessive activation can lead to severe systemic adverse effects like shock syndromes, e.g. allergic shock. The granulocytes, as defined herein, are preferably independently selected from any of eosinophils, neutrophils, basophils and mast cells.

In a special aspect the present invention discloses the treatment of a type I or type III allergy, autoimmune diseases or septic shock with a pharmaceutical preparation comprising escin.

BRIEF DESCRIPTION OF THE DRAWINGS

The present invention is further illustrated by the following figures, without being limited thereto.

DETAILED DESCRIPTION OF THE INVENTION

Figure 1:
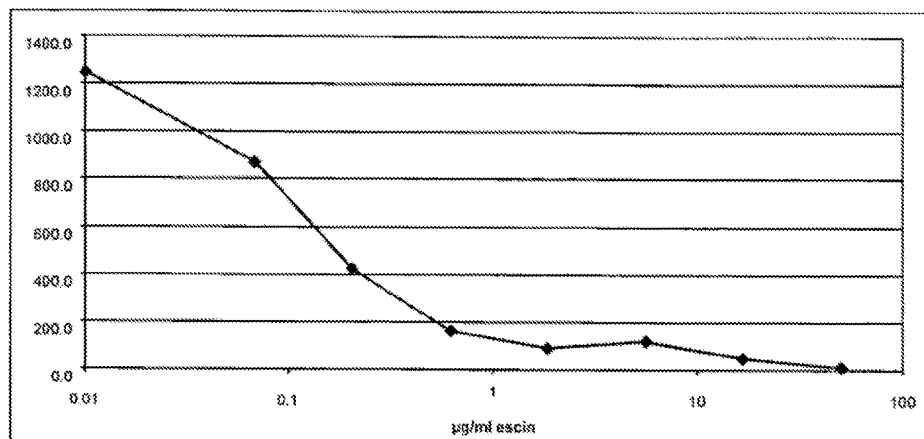
FIG. 1: Inhibition of TNF-alpha production of LPS-stimulated human blood cells. Human blood was incubated with the indicated concentrations of escin. Cells were stimulated with 100 ng/ml LPS (Sigma) and the TNF-alpha in the supernatant was determined with a commercial ELISA Kit (Bender-Med-Systems) after 18 hours of stimulus. The x-axis gives the concentrations of escin in µg/ml, the y-axis gives the concentration of TNF-alpha in pg/ml.

Escin, also called aescin, is a triterpene saponin mixture extracted from the seed of chestnut. It is a component of several pharmaceuticals on the market (in Austria: Reparil from Madaus, Opino from Wabosan, Venosin from Astellas and several more). Often the products contain additional pharmaceutically active compounds such as diethylammoniumsalicylic acid, Buphenin and essential oils. Its primary indication is venous insufficiency based on the inhibitory potential of escin on lysosomal proteins and subsequently the reduced permeability of capillaries. Their anti-inflammatory, anti-oedematous, and venotonic properties, horse-chestnut extracts (HCE) or horse-chestnut seeds extracts (HCSE), standardised to escin, have been studied extensively in preclinical models of CVI and in patients with the disease. A comprehensive overview of the current knowledge on escin as well as the chemical structures of escin has been compiled by Sirtori, Pharmacological Research, Vol. 44 (3) 2001:183-193; the review includes extensive data on the mechanism of action and on the clinical properties of the drug. According to this document beta-escin is the active component of the mixture and is the molecular form present in major available pharmaceutical products. Beta-escin is the preferred form of escin according to the present invention. In addition products containing escin are licensed against traumatic injuries, edema (including edema of the brain), hematoma, bruises, sprain, tendosynovitis, and pain of the spine. Escin is also known as an anti-inflammatory substance, but mainly due to its inhibition of edema. An inhibition of an inflammatory response at cellular level has not been described so far. A detailed review of the use of escin and horse chestnut extracts can be found in: Tiffany at al., Journal of Herbal Pharmacotherapy, Vol. 2(1) 2002:71-85. Also, the antioedematous mechanism of β-escin is still unknown, specially at the molecular level. Besides some speculations about the mechanism of action of this molecule exists, clearly further research is needed.

Recently effects of β-escin on the expression of nuclear factor-κB (NF-κB) and tumor necrosis factor-α (TNF-alpha) after traumatic brain injury in rats was studied (Xiao et al., J Zhejiang Univ SCI 2005 6B(1):28 28-32). The authors found a significant reduction of NF-κB expression level in tissue after traumatic brain injury in rats supporting their claim that escin might be useful in patients with traumatic brain injury. It was found that escin can inhibit NF-κB, itself an activator of proinflammatory TNF-alpha.

According to other sources escin has proinflammatory effects. For example it is used as adjuvant in several pharmaceutical preparations (U.S. Pat. No. 7,049,063, U.S. Pat. No. 7,033,827, U.S. Pat. No. 6,943,236, U.S. Pat. No. 6,894,146, U.S. Pat. No. 6,858,204, U.S. Pat. No. 6,800,746, U.S. Pat. No. 6,759,515, U.S. Pat. No. 6,630,305, U.S. Pat. No. 6,509,448, U.S. Pat. No. 6,504,010). An adjuvant is an agent, which, while not having any specific antigenic effect in itself, may stimulate the immune system, increasing the response to a vaccine. Thus escin has in certain conditions also immunostimmulatory uses.

Instead of treating the symptoms of an allergy (i.e. treating the edema formation or itch) it was surprisingly found that an allergy can be treated with escin at a level prior to the stimulation of the immune system. In mast cells IgE/antigen complexes would provoke TNF-alpha release. Surprisingly mast cell activation (and TNF-alpha release) was also inhibited by escin in mast cells which do not rely on the NF-κB pathway. The treatment with escin results in a selective anti-allergic effect of a different pathway.

Herein it was shown for the first time that escin can successfully be used in the treatment of allergic diseases and more broadly as inhibitor of activated granulocytes exemplified by an LPS induced shock reaction. Escin is for example able to reduce the allergic reaction followed by a stimulus of a complex of Immunoglobulin E (IgE) and the corresponding antigen in vitro. Escin inhibits dose-dependently an LPS-mediated release of TNF-alpha in primary human blood. Furthermore escin dramatically reduces the effect of an immunological shock in an in vivo model and was effectively used to treat an ongoing allergic reaction in a patient suffering from uticaria pigmentosa. Lymphocytes as exemplified by the human T-cell line Jurkat or myeloid cells as exemplified by the murine monocytic cell line DC18 were not inhibited by escin after stimulation (release of either IL-2 or TNF-alpha respectively). Contrary to previous assumptions (Xiao et al., supra) of molecular targets of escin the anti-allergic effect of escin is independent of NF-κB. According to the present invention it was found that escin had still an anti-allergic effect in NF-κB pathway independent mast cells (CFTL12). According to a preferred embodiment the pharmaceutical preparation to be used according to the present invention contains escin as the only granulocyte-inhibiting component, preferably as the only pharmaceutically active agent.

Preferably the allergic disease is a chronic disease or an unwanted hyper-reaction of granulocytes. Escin containing products have been on the market since many years and have an excellent safety profile. Therefore the use of escin either alone or in combination with other drugs is an attractive option for chronic patients.

In a special embodiment the allergic disease is a type I or III allergy, preferably mediated by myeloid cells or granulocytes, or an unwanted reaction of granulocytes.

In further embodiments the medicament is preferably used to treat an allergic disease selected from any one of allergic rhinitis, Urticaria pigmentosa, atopic dermatitis, allergic asthma, food allergy, allergic conjunctivits, allergy of the intestinal or uro-genital tract and an allergy of the ears. In addition, the medicament is preferably used to treat type III allergic diseases or other autoimmune disorders, such as psoriasis, arthritis, immune thrombocytopenia (ITP), autoimmune hemolytic anemia (AHA) and systemic lupus erythematosus (SLE), rheumatoid arthritis (RA), type I diabetes and multiple sclerosis.

In further embodiments the medicament is preferably used to treat skin diseases with an enhanced activation of granulocytes also including diseases complicated by secondary bacterial infections.

Preferably the pharmaceutical preparation is in form of a preparation for topical or mucosal use, preferably skin lotions, cremes, powders, sprays or gargle solutions. The escin preparation is especially suitable for topical application to treat skin or mucosal symptoms of the granulocyte mediated disease such as inflammation. But also systemic, e.g. parenteral or oral (also for specific mucosal treatment), is possible.

In another embodiment the preparation is in form for oral intake, preferably in form of pastilles, tablets, gums, lozenges, powders or drinking solutions. Systemic distribution of escin is especially preferred in cases with systemic granulocyte activation such as an anaphylactic shock or septic shock.

The preparation may also comprise pharmaceutical carriers, excipients, preferably polymeric excipients, or additives. The term "carrier" refers to a diluent, e.g. water, saline, excipient, or vehicle with which the composition can be administered.

For a solid or fluid composition the carriers or additives in the pharmaceutical composition may comprise SiO2, TiO2, a binder, such as microcrystalline cellulose, polyvinylpyrrolidone (polyvidone or povidone), gum tragacanth, gelatine, starch, lactose or lactose monohydrate, alginic acid, maize starch and the like; a lubricant or surfactant, such as magnesium stearate, or sodium lauryl sulphate; a glidant, such as colloidal silicon dioxide; a sweetening agent, such as sucrose or saccharin. Preferably the preparation comprises buffers or pH adjusting agents, e.g. selected from citric acid, acetic acid, fumaric acid, hydrochloric acid, malic acid, nitric acid, phosphoric acid, propionic acid, sulfuric acid, tartaric acid, or combinations thereof. Escin in the form of a pharmaceutically acceptable salt, for example sodium salt may also be used. Other pharmaceutically acceptable salts include, among others, potassium, lithium and ammonium salts. Preferred excipients are polymers, especially cellulose and cellulose derivatives.

Preferably escin is in doses between 0.01 mg per kg of a patient and 500 mg/kg, preferably between 0.1 mg/kg and 100 mg/kg, most preferred between 1 mg/kg and 40 mg/kg. The present invention also provides the use of the pharmaceutical preparations. The administration of the preparation is not limited to administrations at the same time of an allergic reaction but can also be used before or after the reaction, e.g. for prophylactic treatment, i.e. a treatment before an expected exposure to an allergen to reduce the force of the reaction.

EXAMPLES

The present invention is further illustrated by the following examples, without being limited thereto.

Example 1: Escin is Active Against LPS Induced TNF-alpha Release

TNF-alpha is a mediator that is central in an inflammatory process as observed during infections, and autoimmune diseases. It is released by white blood cells, endothelium and several other tissues in the course of damage, e.g. by infection but also during an allergic reaction. Its release is stimulated by several other mediators, such as interleukin 1 and bacterial endotoxin. Cell based assays using human primary blood cells stimulated with lipopolysaccharide demonstrated that escin dose-dependently inhibits TNF-alpha release (FIG. 1.).

Example 2: Escin Prevents TNF-alpha Release from Allergic Stimulated Mast Cells

Figure 2:
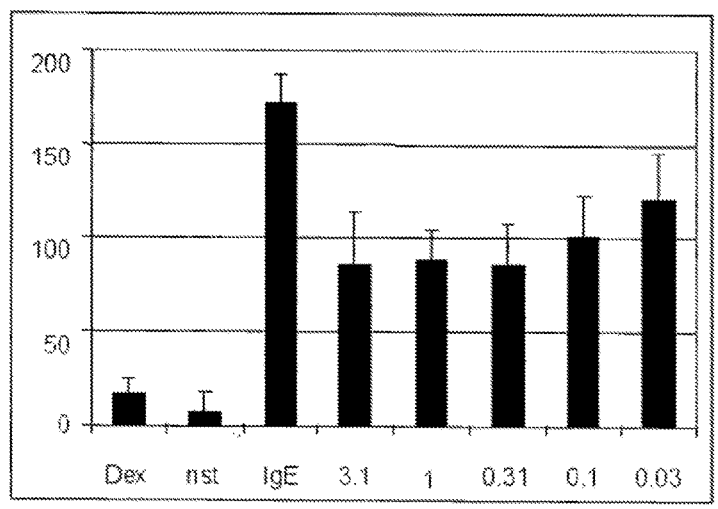
FIG. 2: Inhibition of TNF-alpha production from IgE/antigen stimulated mast cells. CFTL12 Mast cells were incubated with concentrations ranging from 3.1 µM to 0.03 µM β-escin and 0.3 µM Dexamethasone respectively. 60 minutes later cells were stimulated with an IgE/antigen complex. Cells were incubated at 37° C. for 6 hours and TNF-alpha in the supernatant was determined by a commercial mouse TNF-alpha ELISA (Bender-Med-Systems). Error bars indicate the standard deviation between 4 independent wells. 1, dexamethasone; 2, non-stimulated; 3, IgE/Antigen stimulated; 4, 3.1 µM escin; 5, 1 µM escin; 6, 0.31 µM escin; 7, 0.1 µM escin; 8, 0.031 µM escin; 1, and 4-8 were stimulated with IgE/Antigen; y-axis gives the concentration of TNF-alpha in pg/ml.

Murine mast cells stimulated either with IgE and the corresponding antigen respond with the production of several mediators including TNF-alpha which serves as an indicator for the identification of antiallergic substances. Application of escin reduces the release of this mediator in a dose dependent manner. An inhibition of TNF-alpha production of at least 50% was observed at concentrations of 0.31 μM. At a concentration of 30 nM the inhibitory effect was significant. This result indicates that although the inhibitory effect was not as efficient as observed for the control corticosteroid Dexamethasone escin has potent antiallergic properties (FIG. 2).

Figure 3:
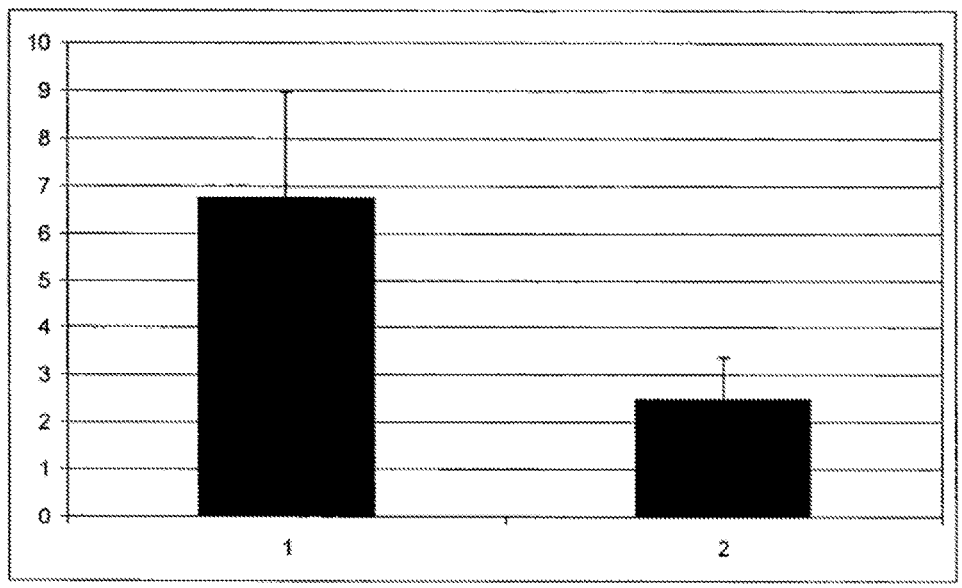
FIG. 3: Balb/c mice (n=8) were treated with 15 mg/kg lipopolysaccharide (Sigma). Mice were simultaneously treated with a single dose of 15 mg/kg β-escin. 1 hour after treatment mice were sacrificed and serum was obtained. Levels of TNF-alpha were determined by using a commercial ELISA-Kit (Bender-Med-Systems). The y-axis reflects the amount of TNF-alpha in mouse serum in ng/ml. Bar 1 indicates the vehicle treated mice and bar 2 shows the result of mice treated with escin.

Example 3: Escin is Active in an In Vivo Animal Model that Mimics the Effect of an Immunological Shock TNF-induction in mice administration of lipopolysaccharide is a well established model for fast immunological reactions and a model for septic shock. As shown in FIG. 3 the treatment of mice with 15 mg/kg of escin reduces the TNF-alpha level to 30%.

Example 4: Treatment of a Patient with Uticaria Pigmentosa with an Allergic Skin Reaction A patient diagnosed with uticaria pigmentosa, a disease that is characterized by unspecific allergic reactions caused by an overreaction of mast cells. The 49 year old female patient had a history of allergic reactions mainly of the skin and in some cases systemic manifestations that were treated with antihistamines and corticosteroids. Prior treatment a strong allergic reaction was ongoing on the skin of large areas of both legs and hands. The patient reported itching and pain of the skin. Clearly the inflammation of the skin was visible. The following score was used in order to measure the severity of the symptoms: 5=full blown reaction including redness of the skin, itching and pain, open wounds partly visible, 4=reduced redness no itching and light pain, wounds closed, 3=redness still visible, absence of pain, 2=skin colour comparable to unaffected areas, symptoms mild, 1=affected areas indistinguishable from healthy areas, wounds are healing, 0=unaffected healthy skin.

Figure 4:
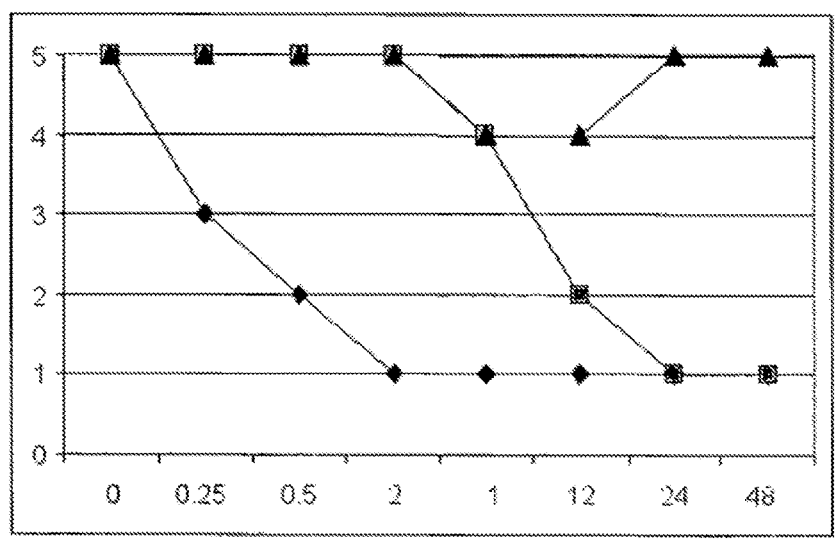
FIG. 4: Symptoms score of a patient with uticaria pigmentosa: A 49 year old patient with uticaria pigmentosa was treated on affected areas of both legs with a gel containing 1.5% escin. The score of symptoms for each area was recorded and documented by digital photography. Treatment for the left leg started at point 0. Diamonds indicate the score of the left leg. Due to the surprising fast response of the left leg the treatment of the right leg was initiated after one hour (quarters). A small area of the skin was left untreated (triangles). X-axis gives the time-points after treatment initiation in hours.

Both legs of the patient were treated with a gel containing 1.5% escin and some formulation excipients. The score of symptoms for each area was recorded and documented by digital photography (FIG. 4). Treatment for the left leg started at point 0.

Due to the surprising and fast response the patient requested a treatment of the second leg that was started after one hour. Again the response was very effective. Affected areas on the skin of the left hand served as a control.

The invention claimed is:

1. A method of treating an allergic rhinitis in a subject having allergic rhinitis, the method comprising:
   topically administering a pharmaceutical composition consisting of escin and a solvent to a mucosa of the subject, wherein the composition is formulated as a spray.
2. The method of claim 1, wherein the subject is a human.
3. The method of claim 1, wherein the solvent is water.
4. The method of claim 1, wherein the escin is beta-escin.
5. A method of treating an allergic rhinitis in a subject having allergic rhinitis, the method comprising:
   topically administering a pharmaceutical composition consisting of escin, a solvent, and one or more of: a carrier, excipient, and additive; and wherein the composition is formulated as a spray.
6. The method of claim 5, wherein the subject is a human.
7. The method of claim 5, wherein the solvent is water.
8. The method of claim 5, wherein the escin is beta-escin.

* * * * *